United States Patent [19]

Sotoya et al.

[11] Patent Number: 5,093,022

[45] Date of Patent: Mar. 3, 1992

[54] BLEACHING COMPOSITION

[75] Inventors: Kohshiro Sotoya; Nobuyuki Ogura, both of Wakayama; Muneo Aoyagi; Moriyasu Murata, both of Tochigi, all of Japan

[73] Assignee: Kao Corporation, Tokyo, Japan

[21] Appl. No.: 441,941

[22] Filed: Nov. 27, 1989

[30] Foreign Application Priority Data

Nov. 30, 1988 [JP] Japan .................. 63-303161

[51] Int. Cl.$^5$ .................. C11D 7/54; C11D 3/395
[52] U.S. Cl. .................. 252/102; 42/186.38; 42/186.29; 42/186.41; 42/94
[58] Field of Search .................. 252/186.38, 186.39, 252/186.41, 94, 102

[56] References Cited

U.S. PATENT DOCUMENTS

| | | | |
|---|---|---|---|
| 4,397,757 | 8/1983 | Bright et al. | 252/186.41 |
| 4,412,934 | 11/1983 | Chung et al. | 252/186.38 |
| 4,483,778 | 11/1984 | Thompson et al. | 252/94 |
| 4,751,015 | 6/1988 | Humphreys et al. | 252/99 |
| 4,778,618 | 10/1988 | Fong et al. | 252/186.23 |
| 4,818,426 | 4/1989 | Humphreys et al. | 252/99 |
| 4,904,406 | 2/1990 | Darwent et al. | 252/102 |
| 4,933,103 | 6/1990 | Aoyagu et al. | 252/186.38 |

FOREIGN PATENT DOCUMENTS 0284292 9/1988 European Pat. Off. .
2226779 12/1972 Fed. Rep. of Germany .

*Primary Examiner*—John S. Maples
*Assistant Examiner*—Shean C. Wu
*Attorney, Agent, or Firm*—Birch, Stewart, Kolasch & Birch

[57] ABSTRACT

A bleaching composition which may serve as a detergent comprises hydrogen peroxide and a bleaching activator having a cationic group and having the formula (I) in which L is an ester-having phenyl and an amide-having phenyl:

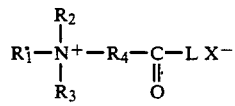

9 Claims, No Drawings

BLEACHING COMPOSITION

BACKGROUND OF THE INVENTION

1. Field of the Invention

The invention relates to a bleaching composition which may serve as a detergent. It contains a bleaching activator having a cationic group.

2. Description of Related Art

Since chlorine type bleaching agents are restricted in the kind of fibers to which they are applicable, can not be used for colored or printed articles and have inherent odores, oxygen type bleaching agents free from such drawbacks have been remarkably popularized recently.

As the oxygen type bleaching agent, sodium percarbonate or sodium perborate has been utilized particularly, in view of bleaching performance and stability.

However, since the oxygen type bleaching agents show poor bleaching power as compared with chlorine type bleaching agents, various kinds of bleaching activators have been used in combination.

Although tetraacetyl ethylenediamine, acetoxybenzene sulfonate, tetraacetyl glycoryluryl, glucose pentacetate, etc. have been used as typical bleaching activators, their bleaching activating effect is not yet sufficient.

U.S. Pat. No. 4,397,757 discloses a bleaching activator of the compound having the thereinafter shown formula (I) in which L is phenyl. It is noted, however, that the reference compound is not so crystalline and therefore is not good at stability at storing.

SUMMARY OF THE INVENTION

The present inventors have made an earnest study for obtaining an oxygen type bleaching type agent and a bleaching detergent of higher bleaching power and, as a result, have accomplished the present invention based on the finding that a specific cationic compound is extremely excellent as the bleaching activator.

That is, the present invention provides a bleaching composition and a bleaching detergent composition containing:

(a) hydrogen peroxide or a peroxide forming hydrogen peroxide in an aqueous solution, and (b) a cationic compound represented by the following general formula (I):

$$R_1-\overset{R_2}{\underset{R_3}{\overset{|}{N^+}}}-R_4-\overset{O}{\underset{}{\overset{\|}{C}}}-L \; X^-$$

where, $R_1$, $R_2$ and $R_3$ each represents an alkyl group, alkenyl group or alkylaryl group, $R_4$ represents an alkylene group, cycloalkylene group, phenylene group or alkylene phenylene group, L represents

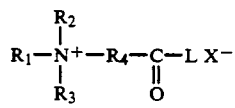

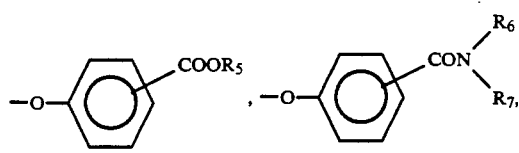

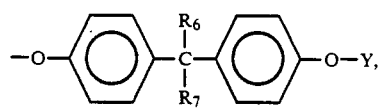

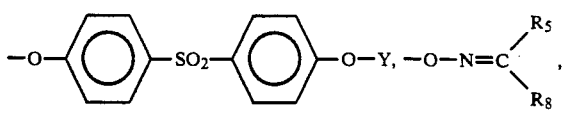

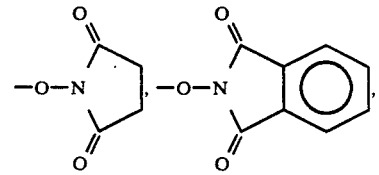

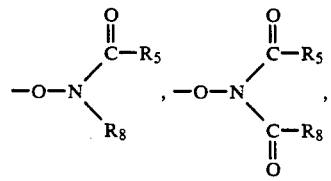

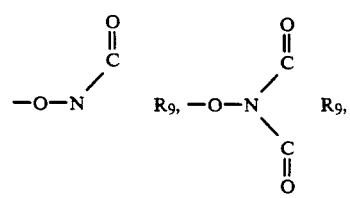

a glycerine residue, or a residue of a saccharide derivative in which $R_5$ and $R_8$ each represents an alkyl group, $R_6$ and $R_7$ each represents H or an alkyl group, $R_9$ represents an alkylene group or alkenylene group, Y represents H or

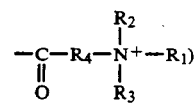

and

X represents an organic or inorganic paired ion.

In the invention, the compound having the formula (I) in which L is specifically defined is improved in view of crystallinity and eventual stability in storing.

These cationic compounds have a splitting group L that is easily disconnected by reaction with hydrogen peroxide, and a bleaching active species formed has a cationic group. Therefore, it is assumed that since the rate of forming the bleaching active species is high and the bleaching active species is present being adsorbed or concentrated at the surface of textile, the bleaching power is remarkably improved.

The groups $R_1$–$R_9$ have 1 to 24 carbon atoms and may be branched or have a substituent such as a hydroxyl group.

It is particularly desirable for such a compound in which $R_1$ represents $C_{1-14}$ alkyl group, $R_2$, $R_3$ each represents $C_{1-2}$ alkyl groups, $R_4$ represents —(CH$_2$)$_{1-5}$—, L represents the structural formulas supra $R_5$ represents $C_{1-2}$ alkyl group, $R_6$ and $R_7$ each represents H or $C_{1-2}$ alkyl group, $R_8$ represents $C_{1-2}$ alkyl group.

In the present invention, as a peroxide forming hydrogen peroxide in an aqueous solution, there can be mentioned, for example, sodium percarbonate, sodium tripolyphosphate-hydrogen peroxide adduct, sodium pyrophosphate-hydrogen peroxide adduct, urea-hydrogen peroxide adduct or $4Na_2SO_4 \cdot 2H_2O_2 \cdot NaCl$, sodium perborate monohydrate, sodium perborate tetrahydrate, sodium peroxide and calcium peroxide. Among them, sodium percarbonate, sodium perborate monohydrate and sodium perborate tetrahydrate are particularly preferred.

The blending ratio between (a) hydrogen peroxide or the peroxide forming hydrogen peroxide in an aqueous solution and (b) the cationic compound represented by the general formula (I) in the bleaching composition and the bleaching detergent composition according to the present invention is usually: (a)/(b) (molar ratio)=99.9/0.1-20/80 and, more preferably, 99/1-50/50.

In the bleaching composition and the bleaching detergent composition according to the present invention, known ingredients usually added to bleaching compositions or bleaching detergent compositions can be added in addition to the above-mentioned essential ingredients. As a builder, for instance, it is possible to use a water soluble inorganic builder such as sulfate, carbonate, hydrogen carbonate, silicate and phosphate, a water insoluble inorganic builder such as zeolite, as well as organic builder such as ethylenediamine tetraacetate, nitrile triacetate, tartarate or citrate. Further, as the stabilizer for the peroxide or the hydrogen peroxide adduct, it is possible to use a magnesium salt such as magnesium silicate, magnesium chloride, magnesium silicon fluoride, magnesium oxide, and magnesium hydroxide and silicate such as sodium silicate. Further, it is also possible to add, if required, an anti-redeposition agent such as carboxymethyl cellulose, polyvinyl pyrrolidone or polyethylene glycol; an anionic surface active agent such as an alkyl sulfate, alkane sulfonate, alkyl ether sulfate, alkyl benzene sulfonate, α-olefin sulfonate and higher fatty acid soap; a nonionic surface active agent such as a polyoxyethylene alkylphenol ether, polyoxyethylene alkyl ether or mono- or diethanol amide of higher fatty acid or amine oxide; an amphoteric surface active agent such as betain; enzyme such as proteasse, lipase, amylase or cellulase; fluorescent improver (whitener) dye, pigment, perfume, etc.

Furthermore, the bleaching composition according to the present invention can properly mixed with known cloth granular detergent to obtain a bleaching detergent composition.

According to the present invention, a bleaching agent and a bleaching detergent composition of higher bleaching effect as compared with the conventional products can be obtained.

DESCRIPTION OF THE PREFERRED EMBODIMENTS

The present invention is to be explained referring to examples but the invention is not limited only to these examples.

REFERENCE EXAMPLE 1

Synthesis of:

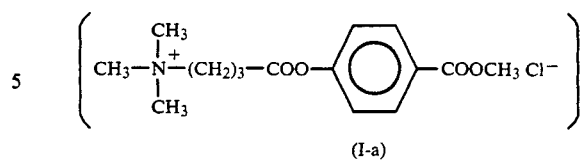

(I-a)

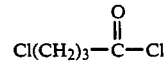

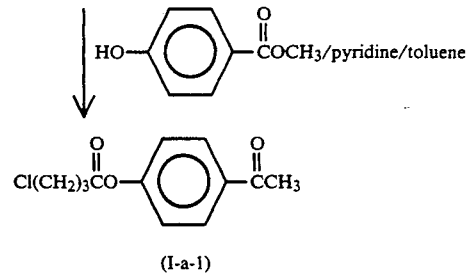

(I-a-1)

In a four-necked flask equipped with a thermometer and a stirrer, 390 g (2.56 mol) of methyl p-hydroxy benzoate was dissolved in one liter of toluene, to which 203 g (2.56 mol) of pyridine was added. When 361.6 g (2.56 mol) of chloro butyric acid chloride was dropped in a water bath (about 20° C.) for one hour and 30 min, pyridine hydrochloride salt as white crystals was precipitated. It was further aged for one hour, and pH was adjusted to 7 with addition of MgO. Then, the solid content was filtered and the filtrate was removed with the solvent under a reduced pressure and then distillated to obtain 589.5 g (90% yield) of a compound (I-a-1) (b.p. 140°-150° C./0.3 mmHg).

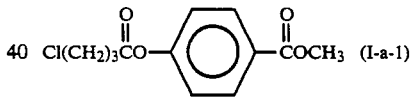

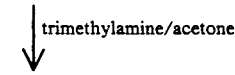

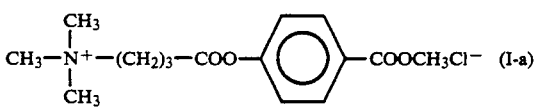

124.0 g (0.433 mol) of the compound (I-a-1) was dissolved in 400 g of an acetone as a solvent in a one liter autoclave and 56.0 g (0.949 mol) of methyl amine was added and reacted for 5 hours at an elevated temperature of 90° C. After the reaction was over, they were extracted from the autoclave, white precipitates were filtered, washed with acetone and then dried to obtain 110.0 g (0.349 mol) of the compound (I-a) as white crystals (72.1% yield).

REFERENCE EXAMPLE 2

Synthesis of:

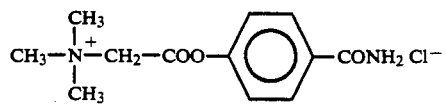

(I-b)

-continued

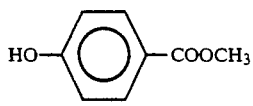

↓ NH₃ aq

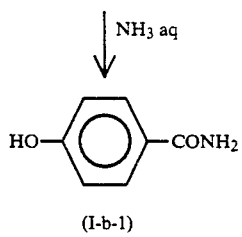
(I-b-1)

Into a one liter autoclave, were charged 200 g (1.32 mol) of methyl p-hydroxy benzoate and 400 g of an aqueous 28% ammonia (6.6 mol). After charging, temperature was elevated to conduct reaction at 130° C. for 10 hours. After the reaction was over, the reaction products were extracted from the autoclave, concentrated under a reduced pressure and then cooled in an ice bath. Deposited crystals were collected by filtration and then dried to obtain 104 g (58% yield) of the compound (1-b-1).

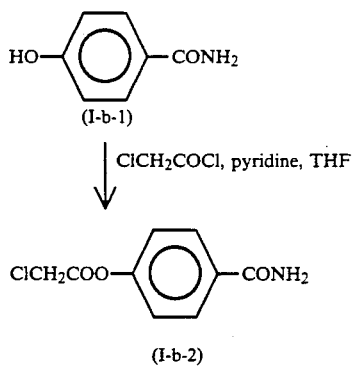

Into a 300 ml four-necked flask, 30 g (0.22 mol) of the compound (I-b-1), 17.4 g (0.22 mol) of pyridine and 200 ml of THF were added, to which 24.8 g (0.22 mol) of chloroacetyl chloride was dropped in an ice bath for 10 min. After stirring as they were for one hour, they were filtered. The resultant precipitates were washed with water to remove pyridine hydrochloride. When the remaining precipitates were washed with a small amount of acetone and then air-dried, 47 g of the compound (I-b-2) was obtained (100% yield).

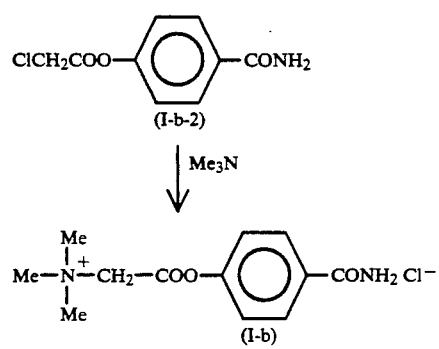

Into a 300 ml egg-shaped flask, 15 g (0.070 mol) of the compound (I-b-2) and 200 ml of acetone were added. 30 ml of an aqueous trimethylamine solution (30%) was heated to 50°–60° C. and evolved gaseous trimethylamine was blown into the flask, which was stirred by a magnetic stirrer at a room temperature for 2 hours. The resultant precipitates were filtered and the precipitates were washed with acetone and then dried to obtain 15.7 g of the compound (I-b) (purity: 94%, yield 77%).

REFERENCE EXAMPLE 3

Synthesis of:

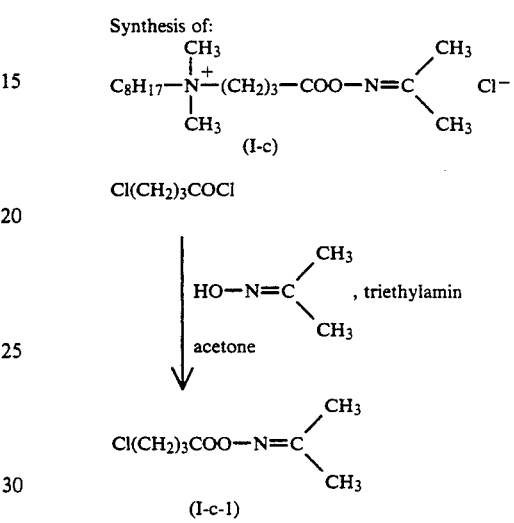

Into a one liter four-necked flask equipped with a thermometer and a cooling tube, were added 73.1 g (1.0 mol) of acetoxime, 101 g (1.0 mol) of triethylamine and 370 ml of acetone. 141 g (1.0 mol) of chloroacetic acid chloride was dropped for one hour while cooling and stirring in an ice bath and, they were stirred further for one hour.

After the reaction was over, the resultant precipitates were filtered and the filtrate was concentrated under a reduced pressure to obtain 117.5 g of the compound (I-c-1) (yield: 100%).

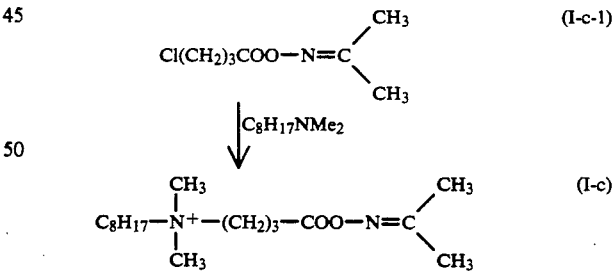

Into a 100 ml four-necked flask equipped with a thermometer and a cooling tube, 15 g (0.084 mol) of the compound (I-c-1) and 14 g (0.089 mol) of dimethyl octyl amine were added, heated by a mantle heater at 100° C. and then stirred for 17 hours. After cooling the reaction mixture, an excess amine was extracted with hexane and removed, and solid contents were collected and dried under a reduced pressure to obtain 22.7 g of the compound (I-c) (92% purity, 74% yield).

REFERENCE EXAMPLE 4

Synthesis of :

-continued

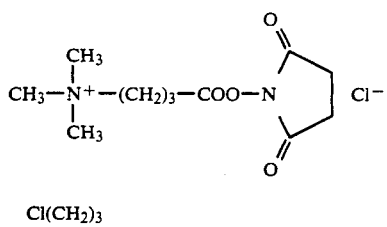

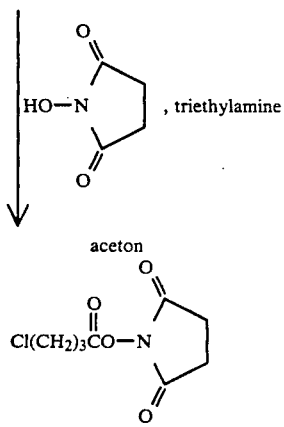

Into a one liter four-necked flask, were charged 80.6 g (0.700 mol) of N-hydroxy succinic acid imide, 300 g of solvent acetone and 70.7 g (0.700 mol) of triethylamine successively in this order and, when 98.7 g (0.700 mol) of chloroacetic acid chloride was dropped and reacted for 2 hours while stirring at a temperature of 10° to 20° C. (under cooling with ice bath), white precipitates (triethylamine hydrochloride salt) were deposited. The precipitates were filtered, and the solvent in the filtrate was distilled off to obtain 152.0 g (99% yield) of the compound (I-d-1).

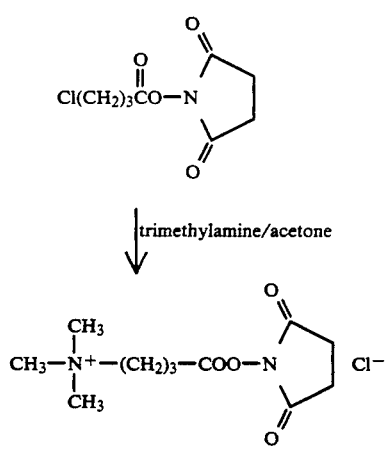

In a 500 cc autoclave, 48.1 g (0.219 mol) of the compound (I-d-1) was dissolved in 200 g of a solvent acetone, to which 12.6 g (0.214 mol) of triethylamine was added temperature was raised and they were reacted at 80° C. for 4 hours. After the reaction was over, the reaction product was extracted from the autoclave and the white precipitates were filtered, washed with acetone and dried to obtain 8.1 g (0.029 mol) of the compound (I-d) as white crystals (13.2% yield).

REFERENCE EXAMPLE 5

Synthesis of:

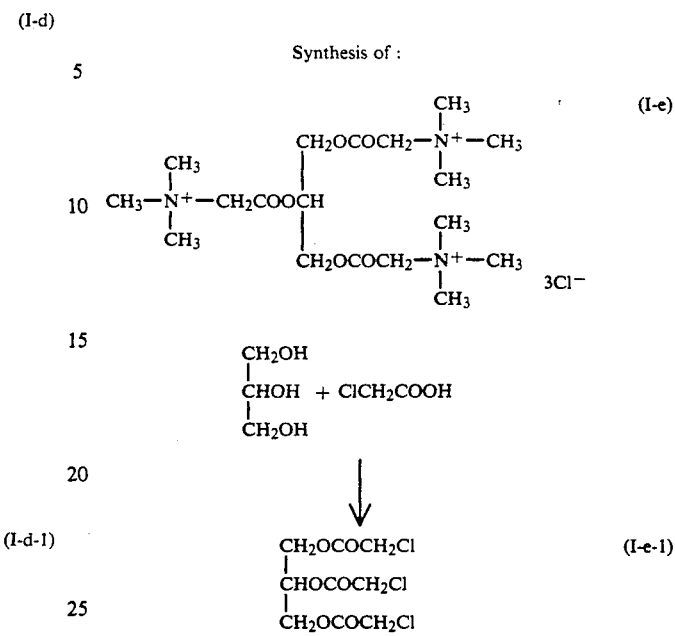

Into a one liter four-necked flask, were charged 50 g (0.5434 mol) of glycerine, 320.9 g (2.7168 mol) of an aqueous 80% solution of ClCH$_2$COOH and 3.7 g of p-toluene sulfonate were charged and reacted while dewatering at 130° C. for 7 hours. After filtering the thus deposited excess ClCH$_2$COOH, 133.7 g of the compound (I-e-1) was obtained by distilling off the resultant liquid (76.5% yield, bp: 206° C./1-2 mmHg).

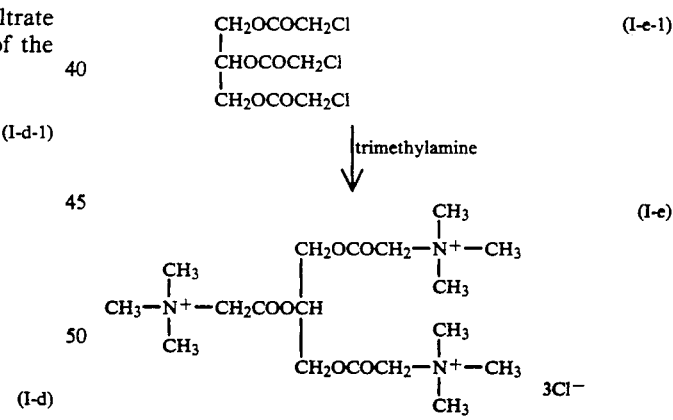

To a 500 ml four-necked flask equipped with a gas introduction tube, 26.0 g (0.081 mol) of the compound (I-e-1) and 150 g of acetone were charged, to which dry triethylamine was blown at a room temperature for 2 hours. After aging at a room temperature for 2 hours, acetone was distilled off under a reduced pressure and then the residue was dried to obtain 24.2 g (60% yield, MW: 498.5) of the compound (I-e) was obtained.

REFERENCE EXAMPLE 6

Synthesis of:

-continued

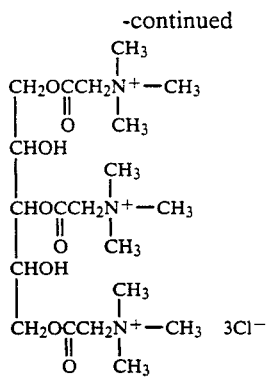

(I-f)

(substituent positions are not clear)

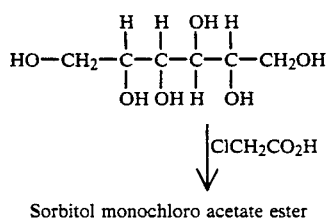

Sorbitol monochloro acetate ester (I-f-1)

To a 200 ml four-necked flask equipped with a thermometer and a dewatering tube, after adding 18.9 g (0.20 mol) of monochloro acetic acid, 36.4 g (0.20 mol) of L-sorbitol and 60 ml of benzene, they were heated under stirring at 120° C., formed water and benzene were distilled off through the dewatering tube and stirring was effected for 12 hours. The reaction mixture was cooled to a room temperature, extracted with chloroform and then washed with water. After drying with magnesium sulfate, the solvent was distilled off under a reduced pressure to obtain 18.1 g of the compound (I-f-1). The average addition mol number was 3.1 mol.

Sorbitol monochloro acetate (I-f-1)

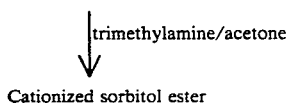

Cationized sorbitol ester (I-f)

To a 100 cc four-necked flask, 5.3 g of the compound (I-f-1) and 30 g of acetone as a solvent were charged, to which 6.0 g (0.1057 mol) of trimethylamine was blown under stirring at a room temperature (25° C.) for 2 hours. When separated from the acetone layer and dried, 5.9 g of the compound (I-f) as white crystals was obtained.

REFERENCE EXAMPLE 7

Synthesis of:

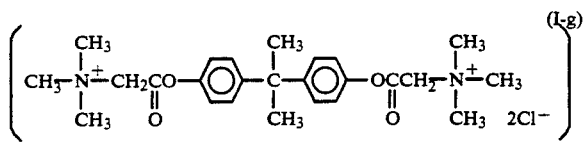

-continued

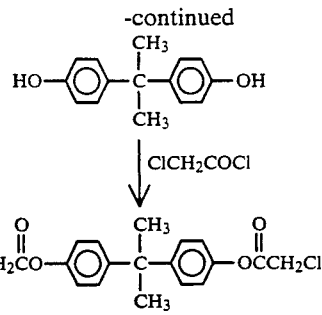

To a one liter four-necked flask equipped with a thermometer and a cooling tube, were added 100 g (0.44 mol) of bisphenol A, 92.9 g (0.92 mol) of triethylamine and 250 ml of acetone, to which 103.9 g (0.92 mol) of chloroacetyl chloride was dropped at a room temperature for one hour and stirred at a room temperature for three hours.

The thus formed precipitates (triethylene amine hydrochloride) were separated by filtration and the filtrate was concentrated to obtain 183 g of the compound (I-f-1) (80% purity, 88% yield).

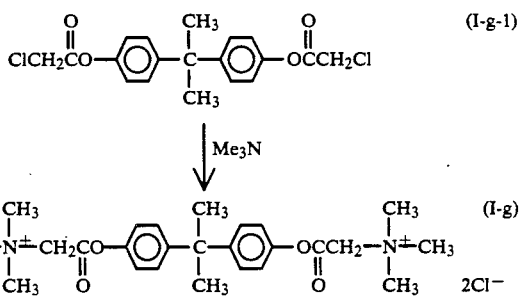

Into a one liter four-necked flask equipped with a thermometer and a cooling tube, 120 g (80% purity, 0.25 mol) of the compound (I-f-1) and 370 ml of acetone were added. After blowing 30 g (0.5 mol) of anhydrous triethylamine into the flask, they were stirred at a room temperature for 12 hours.

The thus formed precipitates were filtered and the precipitates were washed with acetone and then dried to obtain 132 g (92% purity, 96% yield) of the compound (I-g).

EXAMPLE 1

Each of the bleaching compositions of the present invention and comparative products shown in Table-1 was prepared by using the activators I-a to I-g synthesized by the reference examples described above and respective bleaching effects were examined.

Measuring Method for the Bleaching Effect

Sodium percarbonate was dissolved into 300 ml of water at 20° C. such that the effective oxygen content was 0.05%, and the activator was added in an amount of 1/16 equivalent of hydrogen peroxide in the solution. Then, immersion bleaching was conducted for 30 min using five pieces of red tea-stained cloth* prepared by the following methods, and then they were washed with water and dried, and the bleaching rate was determined according to the following equation:

Bleaching Rate for Red-Tea Stained Cloth $$\text{Bleaching ratio}(\%) = \frac{\text{Reflectance after bleaching} - \text{Reflectance before bleaching}}{\text{Reflectance of white cloth} - \text{Reflectance before bleaching}} \times 100$$

The reflectance was measured by NDR-101DP manufactured by Nippon Denshoku Kogyo Co., using 460 nm filter.

\* Method of Preparing Red Tea-Stained Cloth

After boiling 80 g of Nitto red tea (yellow package) with 3 liter of ion exchanged water for about 15 min, it was filtered through de-seized bleached cotton. Then, calico #2003 was immersed in the solution and boiled for about 15 min. They were removed from the heating source, left for about 2 hours and then dried spontaneously, washed with water till the washing liquid was no more colored, dewatered and then pressed into a test specimen of 8 cm×8 cm size, which was served for the test.

EXAMPLE 2

Compounds I-a, I-b, I-c, I-d, I-e, I-f, I-g, and TAED were dissolved to a concentration of 0.0042% into a detergent solution containing 0.0833% of commercially available heavy detergent and 0.0083% of sodium carbonate, with which red-tea stained cloths (8 cm×8 cm: 5 piece) prepared in Example 1 were washed using a turbidometer at 20° C. for 10 min and then washed with water dried and, thereafter, bleaching ratio was determined by the same method as in Example 1.

The results are shown in Table-2.

TABLE 1

| | | Bleaching composition | | | | | | | | |
|---|---|---|---|---|---|---|---|---|---|---|
| | | Products of the invention | | | | | | | Comparative products | |
| | | 1 | 2 | 3 | 4 | 5 | 6 | 7 | 8 | 9 |
| Ingredient composition | Sodium per-carbonate | 85 | 88 | 85 | 87 | 92 | 90 | 88 | 94 | 100 |
| | I-a | 15 | | | | | | | | |
| | I-b | | 12 | | | | | | | |
| | I-c | | | 15 | | | | | | |
| | I-d | | | | 13 | | | | | |
| | I-e | | | | | 8 | | | | |
| | I-f | | | | | | 10 | | | |
| | I-g | | | | | | | 12 | | |
| | Tetra-acetyl ethylene-diamine (TAED) | | | | | | | | 6 | |
| Bleaching ratio (%) | | 41.9 | 42.1 | 38.5 | 40.1 | 32.4 | 30.3 | 41.5 | 23.4 | 15.6 |

TABLE 2

| | activator | Bleaching ratio (%) |
|---|---|---|
| Example | I-a | 15.4 |
| | I-b | 13.1 |
| | I-c | 8.1 |
| | I-d | 11.5 |
| | I-e | 6.9 |
| | I-f | 6.1 |
| | I-g | 12.1 |
| Comparative example | TAED | 1.1 |
| | With no activator | 0.2 |

What is claimed is:

1. A bleaching composition, which comprises:
(a) hydrogen peroxide or a peroxide forming hydrogen peroxide in an aqueous solution; and
(b) a cationic compound represented by the following general formula (I)

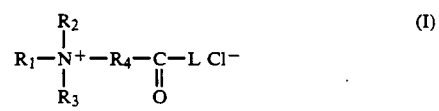

where,
$R_1$ represents a $C_{1-8}$ alkyl group,
$R_2$ and $R_3$ each represent a methyl group,
$R_4$ represents $-CH_2)_{1-5}$,
L represents:

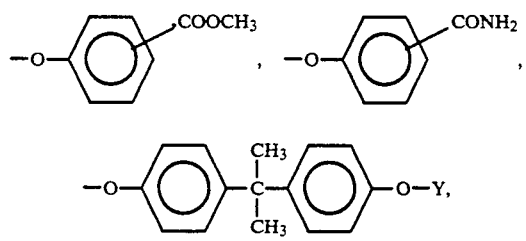

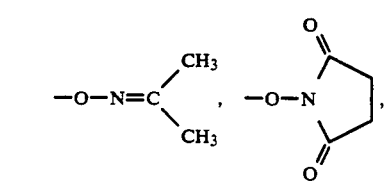

a glycerin residue, or a sorbitol residue, in which Y represents H or

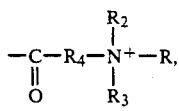

a glycerine residue, or a residue of a saccharide derivative.

2. A bleaching composition according to claim 1, which comprises:

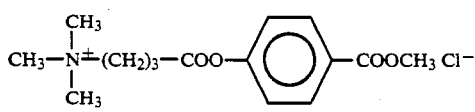

3. A bleaching composition according to claim 1, which comprises:

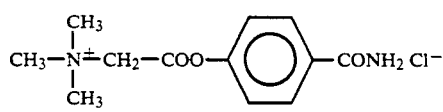

4. A bleaching composition according to claim 1, which comprises:

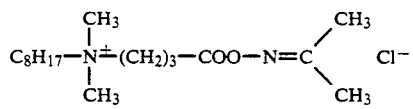

5. A bleaching composition according to claim 1, which comprises:

6. A bleaching composition, which comprises:

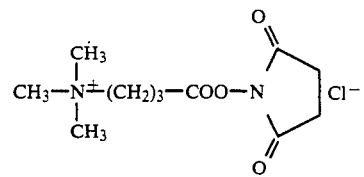

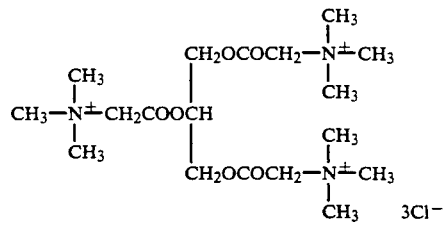

7. A bleaching composition, which comprises:

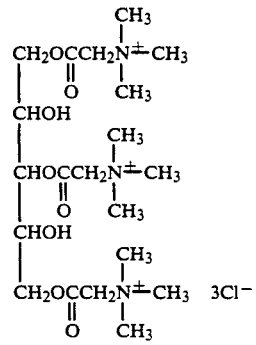

8. A bleaching composition, which comprises:

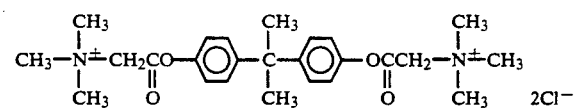

9. A bleaching composition according to any one of claims 2-8 or 1, further comprising a detergent.

* * * * *